US007713515B2

(12) United States Patent
Englebienne et al.

(10) Patent No.: US 7,713,515 B2
(45) Date of Patent: May 11, 2010

(54) METHODS AND COMPOSITIONS FOR USE IN DIAGNOSING AND CHARACTERIZING DISEASES INVOLVING ABNORMAL APOPTOSIS

(75) Inventors: Patrick Englebienne, Zingem (BE); Kenny De Meirleir, Mechelen (BE); Charles Vincent Herst, Oakland, CA (US)

(73) Assignee: R.E.D. Laboratories N.V., Zellik (BE)

( * ) Notice: Subject to any disclaimer, the term of this patent is extended or adjusted under 35 U.S.C. 154(b) by 1390 days.

(21) Appl. No.: 10/855,879

(22) Filed: May 26, 2004

(65) Prior Publication Data

US 2005/0019756 A1    Jan. 27, 2005

Related U.S. Application Data

(60) Provisional application No. 60/473,690, filed on May 27, 2003.

(51) Int. Cl.
*A61K 49/00* (2006.01)

(52) U.S. Cl. .................................................. 424/9.1
(58) Field of Classification Search .................... None
See application file for complete search history.

(56) References Cited

FOREIGN PATENT DOCUMENTS

WO    WO 01/88543    11/2001

OTHER PUBLICATIONS

Dockrell Journal of Infection 2001;42:227-234.*
Liu et al. "Induction of Capase-dependent apoptosis in cultured cells by the Avian Coronavirus Infection Bronchitis Virus" Journal of Virology, 2001, vol. 75, No. 14, pp. 6402-6409.*
Roelens et al. "G-Actin Cleavage Parallels 2-5A-Dependent RNase L Cleavage in Peripheral Blood Mononuclear Cells-Relevance to a Possible Serum-Based Screening Test for Dysregulations in the 2-5A Pathway," (2001) *Innovations in Chronic Fatigue Syndrome Research and Clinical Practice*, 8:63-82.
Potter et al. "Calpain Regulates Actin Remodeling During Cell Spreading," (1998) *The Journal of Cell Biology*, 141:647-662.
Goldschmidt-Clermont et al. "Gc (Vitamin D-Binding Protein) Binds The 33.5 K Tryptic Fragment of Actin," (1986) *Life Sciences*, 38:735-742.
Silverman, Robert H. "Implications for RNase L in Prostate Cancer Biology," (2003) *Biochemistry*, 42(7) 1805-1812.
Prados et al. "Circulating α-Actin in Non-Insulin-Dependent Diabetics With Autonomic Dysfunction," (1995) *International Journal of Cardiology*, 51:127-130.
Drosten et al. "Identification of A Novel Coronavirus in Patients with Severe Acute Respiratory Syndrome," (2003) *The New England Journal of Medicine*, 348:1967-1976.
Ksiazek et al. "A Novel Coronavirus Associated With Severe Acute Respiratory Syndrome," (2003) *The New England Journal of Medicine*, 348-1953-1966.
Laxminarayana et al. "Activation of Caspases and p53 by Bovine Herpesvirus 1 Infection Results in Programmeed Cell Death and Efficient Virus Release," Journal of Virology (1999) 73(5):3778-3788.
Yang F, et al. "Antibody to Caspase-Cleaved Action Detects Apaptosis in Differentiated Neuroblastoma and Plaque-Associated Neurons and Microglia in Alzheimer's Disease" American Journal of Pathology, Philadelphia, PA, USA, vol. 152, No. 2, Feb. 1998, pp. 379-389, XP009037701 ISSN:0002-9440.
Cytoskeleton, Inc.: "G-actin/F-actin in vivo assay kit" 1993, Denver, Colorado, USA XP002473343.

* cited by examiner

*Primary Examiner*—Karen Cochrane Carlson
*Assistant Examiner*—Bin Shen
(74) *Attorney, Agent, or Firm*—Bret E. Field; Bozicevic, Field & Francis LLP

(57) ABSTRACT

Methods are provided for diagnosing and/or characterizing disease involving abnormal levels of cellular apoptosis activity in a subject. In the subject methods, a sample is obtained from a subject suspected of having or known to have a disease involving abnormal levels of cellular apoptosis. The sample is then assayed for the presence of low molecular weight Actin protein fragments. The assay results are used to diagnose the presence of disease involving abnormal levels of cellular apoptosis activity and/or characterize disease involving abnormal levels of cellular apoptosis activity in the subject, e.g. to confirm an initial disease involving abnormal levels of cellular apoptosis diagnosis, to determine the stage of the disease, to monitor disease progression, to predict disease attacks, and the like. Also provided by the subject invention are kits for practicing the methods.

3 Claims, 1 Drawing Sheet

FIGURE 1

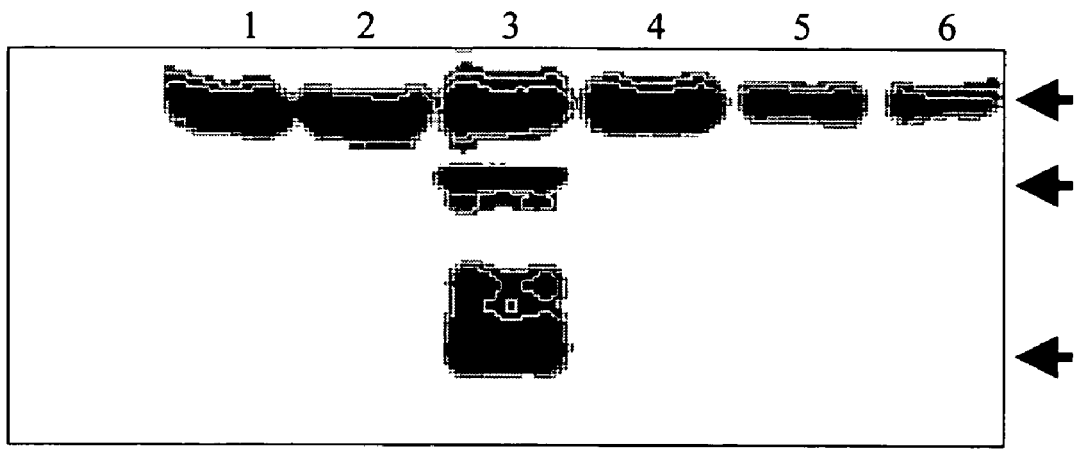

| Figure 1 | A Densitometric Scan of a Western Blot of Actin Protein and Actin Protein Fragments Present in Serum |
|---|---|

Lane 1 -    Patient #1 Serum
Lane 2 -    Patient #2 Serum
Lane 3 -    Patient #3 Serum
Lane 4 -    Patient #4 Serum
Lane 5 -    Normal Control Serum
Lane 6 -    0.5 microgram purified native Actin protein Top arrow:    42 kDa molecular weight native Actin protein
Middle arrow: 27 kDa molecular weight Actin protein fragment
Bottom arrow: 15 kDa molecular weight Actin protein fragment

METHODS AND COMPOSITIONS FOR USE IN DIAGNOSING AND CHARACTERIZING DISEASES INVOLVING ABNORMAL APOPTOSIS

CROSS REFERENCE TO RELATED APPLICATIONS

Pursuant to 35 U.S.C. §119 (e), this application claims priority to the filing date of the U.S. Provisional Patent Application Ser. No. 60/473,690 filed May 27, 2003; the disclosure of which are herein incorporated by reference.

INTRODUCTION

Background of the Invention

When a microorganism invades the body, the immune system is activated in order to fight the infection. The cells of the immune system produce a variety of chemical messengers, some of which direct the activities of specialized cells in order to attack and kill infected cells and/or to induce such cells to commit suicide.

An infected cell that is attacked directly (e.g., by a cytotoxin or macrophage) undergoes a process of necrosis, whereas an infected cell induced to commit suicide undergoes a process of apoptosis. Both pathways lead ultimately to the death of the cell and the release of cellular fragments into the circulation. In turn, these fragments induce the inflammatory process to occur, the hallmark symptom of which is fever. It is at this stage, typically, that the infection goes from being covert (i.e., no symptoms) to overt (i.e., symptoms apparent).

Individuals who come in contact with persons or materials infected with microbes such as viruses and bacteria would benefit from early diagnosis of the infection, well before the inflammatory process began (i.e., during the earliest phases of the immune response). Indeed the detection of such abnormal cellular activation would allow earlier diagnosis, earlier treatment and reduce the likelihood of transmission of infection from person to person.

Actin is a protein present in every cell. The monomeric form of the protein (called G-Actin) forms a polymer (i.e., self-complexes) to form long filaments (called F-Actin). These filaments are a major component of the cell's architecture (referred to as the cytoskeleton), and along with other proteins, give the cell a consistent, controllable shape, and allow movement (motility) that is critical for cells involved in catching and killing foreign invaders.

When a cell is wounded or killed (necrosis) or induced to commit suicide (apoptosis), one of the first cellular proteins to undergo degradation is Actin. Actin protein is cleaved into fragments by a number of inflammatory enzymes (e.g., elastase), and these fragments are released into the circulation. Therefore the presence of increasing levels of Actin protein (and Actin protein fragments) in the serum is indicative of an abnormal rate of cellular degradation.

Relevant Literature

Potter, D., et al., J. Cell. Biol. 141(3):647-662 (1998); Goldschmidt-Clermont, P., et al., Life Sciences 38:735-742 (1986); Roelens, S., et al., Journal of Chronic Fatigue Syndrome 8:63-82 (2001); Silverman, R., Biochemistry 42:1805-1812 (2003); Prados, J., et al., Int. J. Cardiol. 51:127-130 (1995); Drosten, et al., N. Engl. J. Med. 165: 1201-1212 (2003); Ksiazek, T., et al., N. Engl. J. Med. 165: 1212-1223 (2003).

SUMMARY OF THE INVENTION

Methods are provided for diagnosing and/or characterizing diseases involving abnormal levels of cellular apoptotic activity in a subject. In the subject methods, a sample is obtained from a subject suspected of having or known to have a disease involving abnormal levels of cellular apoptosis. The sample is then assayed for the presence of low molecular weight Actin protein fragments. The assay results are used to diagnose the presence of disease involving abnormal levels of cellular apoptosis activity and/or characterize disease involving abnormal levels of cellular apoptotic activity in the subject, e.g. to confirm the initial diagnosis of disease involving abnormal levels of cellular apoptotic activity, to determine the stage of the disease, to monitor disease progression, to predict disease attacks, and the like. Also provided by the subject invention are kits for practicing the methods.

BRIEF DESCRIPTION OF THE FIGURES

FIG. 1 represents a densitometric scan of a Western blot detecting Actin protein and Actin protein fragments. Native G-Actin is clearly visible at 42 kDa as are the fragments (the native Actin protein, 27 kDa Actin protein fragment, and 15 kDa Actin protein fragment are indicated with arrows).

DESCRIPTION OF THE SPECIFIC EMBODIMENTS

Methods are provided for diagnosing and/or characterizing disease involving abnormal levels of cellular apoptotic activity in a subject. In the subject methods, a sample is obtained from a subject suspected of having or known to have a disease involving abnormal levels of cellular apoptosis. The sample is then assayed for the presence of Actin protein and/or one or more low molecular weight Actin protein fragments. The assay results are used to diagnose the presence of disease involving abnormal levels of cellular apoptotic activity and/or characterize disease involving abnormal levels of cellular apoptotic activity in the subject, e.g. to confirm an initial diagnosis of disease involving abnormal levels of cellular apoptosis, to determine the stage of the disease, to monitor disease progression, to predict disease attacks, and the like. Also provided by the subject invention are kits for practicing the methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms 'a,' 'an,' and 'the' include plural reference unless the context clearly dictates otherwise. Unless defined otherwise, all technical and scientific terms used herein have the same meaning as commonly understood to one of ordinary skill in the art to which this invention belongs.

As summarized above, the subject invention provides a method of diagnosing the presence of a disease involving abnormal levels of cellular apoptosis in a host. In other words, the subject invention provides a means for determining whether a host is suffering from a disease involving abnormal levels of cellular apoptosis. By "disease involving abnormal levels of cellular apoptosis" is meant a disease that is characterized by the presence of abnormal, e.g., elevated, levels of cellular apoptosis, as compared to non-disease condition. In certain embodiments, the subject invention provides a method of determining whether a host is suffering from an infection, i.e., infectious disease, elicited by an agent that causes a disease involving abnormal levels of cellular apoptosis. Such a disease may include both chronic and acute infectious diseases, where representative infectious diseases include, but are not limited to: Hepatitis B, Hepatitis C, HIV, Severe Acute Respiratory Syndrome (SARS) etc. Another type of disease of interest that involves abnormally elevated levels of cellular apoptosis is chronic immune disease, where representative chronic immune diseases of interest include, but are not limited to: cancer; CFS, MS, lupus, rheumatoid arthritis, Type I diabetes, etc. Conversely, another "disease involving abnormal levels of cellular apoptosis" is cancer, whereby abnormally low levels of cellular apoptosis may be the result of a suppression of the immune system surveillance mechanism, allowing the cancer to grow unchecked in the host.

In determining whether a host suffers from a disease involving abnormal levels of cellular apoptosis, a sample from the host is assayed for the presence of Actin protein and/or one or more low molecular weight fragments of Actin protein. More specifically, a sample of the host is assayed for the presence of G-Actin protein and/or one or more low molecular weight fragments of G-Actin protein. By low molecular weight Actin protein fragment is meant a polypeptide that has a sequence of amino acid residues found in full length Actin protein, where this sequence is at least about 10, usually at least about 20 and more usually at least about 50 residues long and is often longer, where the polypeptide has a molecular weight that is less than that molecular weight of full length Actin protein, i.e. where the polypeptide has a molecular weight that is less than about 42 kDa, as measured by SDS-PAGE (see the experimental section, infra.) Specifically, the sample is assayed for low molecular weight Actin protein fragments ranging in weight from about 5 to 37 kDa, usually from about 15 to 30 kDa and more usually from about 24 to 28 kDa. Of particular interest is the identification of Actin protein fragments having the following molecular weights as determined by SDS-PAGE: 15 kDa and 27 kDa. Representative samples and assay methods for identifying the presence of, and amounts of, low molecular weight Actin protein fragments are described in greater detail infra.

The presence or absence of the low molecular weight Actin protein fragment(s) is then used to diagnose whether or not the host suffers from a disease involving abnormal levels of cellular apoptosis. In other words, the presence or absence of Actin protein and/or low molecular weight Actin protein fragment(s) in the sample is used to determine whether or not the host suffers from a disease involving abnormal levels of cellular apoptosis, such as a microbial infection. For example, in one embodiment, the presence of one or more low molecular weight Actin protein fragments is used to determine whether the host suffers from SARS. Likewise, in another embodiment, quantifying the level of Actin protein and Actin protein fragments may be used to determine whether a host suffers from cancer. As part of the diagnosis, one may also evaluate the subject for other symptoms of the disease of interest that is to be diagnosed, e.g. the additional clinical symptoms described in the background section, supra, as well as in other parts of this application.

Also provided by the subject invention are methods of characterizing the disease involving abnormal levels of cellular apoptosis activity, e.g. SARS disease activity, in a subject suspected of having, or known to have, a disease involving abnormal levels of cellular apoptosis, e.g. SARS. Subjects suspected of having, or known to have, a disease involving abnormal levels of cellular apoptosis and thus amenable to the subject methods can be identified using any convenient protocol. One convenient protocol is diagnosis based on clinical symptoms. A number of different clinical symptoms may be used to identify subjects that may have or have the disease involving abnormal levels of cellular apoptosis of interest, where the specific symptoms employed will necessarily depend on the specific disease involving abnormal levels of cellular apoptosis. For example, where the disease involving abnormal levels of cellular apoptosis of interest is SARS, clinical symptoms of interest include dry cough, fever, dyspnea, headache and hypoxemia The presence of one or more of the above symptoms may be used to identify subjects suspected of suffering from SARS, respectively. Other assays may also be employed, including cell culture, detecting antibodies specific for the infectious agent, detecting nucleic acids of a sequence specific for the infectious agent, etc. The first step of the subject methods is to obtain a suitable sample from the subject or patient of interest, i.e. a patient suspected of having or known to have the disease involving abnormal levels of cellular apoptosis of interest, e.g. SARS. The sample is derived from any initial source that contains native Actin protein and the low molecular weight Actin protein fragments (if present). Sample sources of interest include, but are not limited to, many different physiological sources, e.g. CSF, urine, saliva, tears, tissue derived samples, e.g. homogenates, and blood or derivatives thereof.

In many embodiments, the sample is derived from cells that comprise the Actin protein fragments of interest, if present—i.e. if the patient from which the cells are derived has disease involving abnormal levels of cellular apoptosis. In other embodiments, the sample may be derived from fluids into which the proteins of interest have been released, e.g. are present. In many embodiments, a suitable initial source for the patient sample is blood. As such, the sample employed in the subject assays of these embodiments is generally a blood-derived sample. The blood-derived sample may be derived from whole blood or a fraction thereof, e.g. serum, plasma, etc., where in many embodiments the sample is derived from blood allowed to clot and the serum separated and collected to be used to assay. In certain situations, the sample may be treated to displace Actin protein fragments from Actin protein transport proteins, where any convenient treatment protocol may be employed, e.g. acidification, etc.

In these preferred embodiments in which the sample is a serum derived sample, the sample is generally a fluid-derived sample. Any convenient methodology for producing a fluid serum sample may be employed. In many embodiments, the method employs drawing venous blood by skin puncture (e.g., finger stick, venipuncture) into a clotting or serum separator tube, allowing the blood to clot, and centrifuging the serum away from the clotted blood. The serum is then collected and stored until assayed. Once the patient derived sample is obtained, it is assayed for the presence or absence of one or more low molecular weight Actin protein fragments, either directly or indirectly. The low molecular weight Actin protein fragments of interest are those having a molecular weight ranging from about 5 to 37 kDa, usually from about 15 to 30 kDa and specifically of about 24 to 28 kDa, as determined under SDS-PAGE reducing conditions, as described above, with specific fragments of interest being those having the following molecular weights: 15 kDa and 27 kDa.

The sample may be assayed for the presence or absence of the low molecular weight Actin protein fragments using any convenient methodology. In many embodiments, such methodology involves the following two steps: (a) fractionation of the sample in a manner sufficient such that the one or more Actin protein fragments and the native Actin protein (if present) are present in different fractions, i.e. separating the low molecular weight fragments from each other and from the native Actin protein; and (b) detection of the low molecular weight fragments in the specific fractions, i.e. assaying each fraction for the presence or absence of an Actin protein fragment, where the detection may be qualitative, semi-quantitative or quantitative, and is usually at least semi-quantitative (i.e. not just qualitative). In these embodiments, fractionation may be accomplished using any convenient methodology. The fractionation technique employed may or may not employ native or non-denaturing conditions. Whether fractionation is carried out under denaturing or non-denaturing conditions depends on the particular manner in which the low molecular weight fragments are detected, e.g. whether or not a non-denatured form is required for detection, where representative detection methods are described in greater detail below. Typically, the non-denaturing conditions are 'native' conditions. By 'native' conditions is meant fractionation by a process that substantially preserves the conformation and folding of the low molecular fragment species in the sample. Native conditions are those conditions that do not denature proteins. A variety of non-denaturing fractionation means are known to those of skill in the art, where one means of interest is gel filtration high performance liquid chromatography. Alternatively, fractionation may be carried out under non-native, e.g. denaturing conditions, such as SDS-PAGE (sodium dodecylsulfate-polyacrylamide gel electrophoresis). As the fractionating step involves separating the various low molecular weight Actin protein fragments, fractionation results in the production of one or more fractions that putatively contain the low molecular Actin protein fragment (i.e. is suspected of containing a low molecular weight fragment). As discussed above, the sample or fraction(s) thereof are assayed for the presence or absence of low molecular weight Actin protein fragments, where the assay may be a direct assay or an indirect assay. By direct assay is meant an assay that provides for a direct detection of low molecular weight Actin protein fragments, e.g., an assay yield direct information regarding the presence and often amount of low molecular weight Actin protein fragments in sample, e.g. an assay where an Actin protein specific antibody is employed to detect low molecular weight Actin protein fragments in an appropriately fractionated sample. By indirect assay is meant an assay that detects the presence or absence of low molecular weight Actin protein fragments through detection, usually quantitation, of another species, e.g. native Actin protein and total Actin protein species (e.g., where a relative amount of native Actin protein to total Actin protein species in a sample is determined, from which the presence of low molecular weight Actin protein fragments is indirectly determined). Another type of indirect assay would be an assay that does not differentiate between the various sizes of Actin protein fragments but quantifies the total amount of Actin proteins (i.e., native Actin protein and Actin protein fragments, if any) present in the specimen. This value is then compared to a normal range of values of 'total Actin protein species' present in the specific bodily fluid used as the specimen. Normal ranges may be established for any bodily fluid wherein Actin protein and Actin protein fragments may be detected. As such, the assay employed may or may not also include a determination of the amount of native or full length Actin protein, i.e. Actin protein having a molecular weight of 42 kDa or higher, in the sample.

Any convenient assay protocol may be employed. Suitable assays that may be employed include antibody-based assays, e.g. Western blot assays, such as those described in the experimental section infra. Antibody based assays require the use of antibodies specific for the Actin protein fragments and native Actin protein. The assays may be direct assays, i.e., those which employ antibodies specific for low molecular weight Actin protein fragments. Alternatively, the assays may be indirect assays, i.e., those that detect native Actin protein and total amounts of Actin protein species in a sample, e.g., an assay in which antibodies specific for the C- and N-termini of the native Actin protein are employed.

Antibodies that specifically bind to the subject Actin protein and low molecular weight fragments thereof can be prepared using a variety of convenient methods known to those of skill in the art. See Guide to Protein Purification, supra, as well as Antibodies, A Laboratory Manual (Harlow & Lane eds. Cold Spring Harbor Press, 1988). The antibodies may be polyclonal or monoclonal antibodies depending on the nature of the intended use, as long as they are specific for one or more forms of Actin protein or fragments thereof of interest.

For preparation of polyclonal antibodies, the first step is immunization of the host animal with Actin protein or an immunogenic fragment, including fragment derivative thereof, where the Actin protein immunogen will preferably be in substantially pure form, comprising less than about 1% contaminant. The immunogen may comprise complete Actin protein, fragments or derivatives thereof. To increase the immune response of the host animal, the immunogen may be combined with an adjuvant, where suitable adjuvants include alum, dextran, sulfate, large polymeric anions, oil & water emulsions, e.g. Freund=s adjuvant, Freund=s complete adjuvant, and the like. The immunogen may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The immunogen is administered to the host, usually intradermally, with an initial dosage followed by one or more, usually at least two, additional booster dosages. Following immunization, the blood from the host is collected, followed by separation of the serum from the blood cells. The Ig present in the resultant antiserum may be further fractionated using known methods, such as ammonium salt fractionation, DEAE chromatography, and the like.

As with the preparation of polyclonal antibodies, the first step in preparing monoclonal antibodies specific for Actin protein and fragments thereof is to immunize a suitable host, where suitable hosts include rats, hamsters, mice and the like, and are preferably mice. The Actin protein immunogen, which as above, may be the entire Actin protein or a fragment or derivative thereof, is administered to the host in any convenient manner, where such methods include: subcutaneous injection with adjuvants, nitrocellulose implants comprising the immunogen, intrasplenic injections, and the like, where the immunization protocol may be modulated to obtain a desired type of antibody, e.g. IgG or IgM, where such methods are known in the art. Following immunization, plasma cells are harvested from the immunized host, where sources of plasma cells include the spleen, lymph nodes and the like, with the spleen being preferred. The plasma cells are then immortalized with myeloma cells to produce hybridoma cells; A variety of myeloma cell lines are available and known to those of skill in the art. The plasma and myeloma cells are fused by combining the cells in a fusion medium usually in a ratio of about 10 plasma cells to 1 myeloma cell, where suitable fusion mediums include a fusion agent, e.g. PEG 1000, and the like. Following fusion, the fused cells are selected, e.g. by growing on HAT medium. Following hybridoma cell production, culture supernatant from individual hybridomas is screened for reactivity with Actin protein using standard techniques, where such screening techniques include ELISA, dot blot immunoassays and the like. The antibody may be purified from the supernatants or ascites fluid by conventional techniques, e.g. affinity chromatography Actin protein bound to an insoluble support, protein A sepharose and the like.

Antibodies specific for Actin protein are known in the art, and include those deposited at the American Type Culture Collection under the following accession numbers: 5483 RE; 5462 RE; 9190 RE; 9197 RE; 10406 RE; etc.

The above prepared or obtained antibodies may be modified in a number of different ways to optimize their utility for use in a particular immunoassay. For example, antibody fragments, such as Fv, $F(abN)_2$ and Fab may be prepared by cleavage of the intact protein, e.g. by protease or chemical cleavage.

The antibodies, fragments or derivatives thereof may also be labeled in order to facilitate detection. A variety of protein labeling schemes are known in the art and may be employed, the particular scheme and label chosen being the one most convenient for the intended use of the antibody, e.g. immunoassay. Examples of labels include labels that permit both the direct and indirect measurement of the presence of the antibody. Examples of labels that permit direct measurement of the antibody include radiolabels, such as $^3H$ or $^{125}I$, fluorescers, dyes, beads, chemilumninescers, colloidal particles, and the like. Examples of labels which permit indirect measurement of the presence of the antibody include enzymes where a substrate may provide for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that is conjugated to the enzyme, e.g. the antibody may be covalently bound to biotin and the enzyme conjugate to streptavidin. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In immunoassays of the subject invention, a number of different immunoassay formats are known in the art and may be employed. Representative assay formats include Western blots on protein gels or protein spots on filters, where the antibody is labeled as described above, as is known in the art. For a representative example of a Western blot assay for the presence of Actin protein and fragments thereof in a sample, see the experimental section infra.

Other immunoassays include those based on competitive formats, as are known in the art. One such format would be where a solid support is coated with Actin protein. Labeled antibody is then combined with the patient derived sample suspected to produce a reaction mixture which, following sufficient incubation time for binding complexes to form, is contacted with the solid phase bound Actin protein. The amount of labeled antibody which binds to the solid phase will be proportional to the amount of Actin protein or fragments thereof in the sample, and the presence of Actin protein and fragments thereof may therefore be detected. Other competitive formats that may be employed include those where the sample suspected of comprising Actin protein fragments is combined with a known amount of labeled Actin protein fragments and then contacted with a solid support coated with antibody specific for Actin protein fragments. Such assay formats are known in the art and further described in both Guide to Protein Purification, supra, and Antibodies, A Laboratory Manual, supra. Sandwich-format assays may also be employed. A sandwich assay is performed by initially attaching a first of the two types of antibodies to an insoluble surface or support. This first antibody may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently. The insoluble supports may be any compositions to which antibodies or fragments thereof can be bound, which is readily separated from soluble material, and which is otherwise compatible with the overall method of measuring Actin protein in the sample. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples. Before adding patient samples or fractions thereof, the non-specific binding sites on the insoluble support i.e. those not occupied by the first antibody, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used. Samples, fractions or aliquots thereof are then added to separately assayable supports (for example, separate wells of a microtiter plate) containing support-bound allergen. Preferably, a series of standards, containing known concentrations of Actin protein is assayed in parallel with the samples or aliquots thereof to serve as controls. Generally from about 0.001 to 1 ml of sample, diluted or otherwise, is sufficient, usually about 0.01 ml sufficing. Preferably, each sample and standard will be added to multiple wells so that mean values can be obtained for each. The incubation time should be sufficient for Actin protein molecules to bind the insoluble first antibody. Generally, from about 0.1 to 3 hr is sufficient, usually 1 hr sufficing. After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample. After washing, a solution containing the second specific antibody is applied. The second antibody may be labeled, as described above, to facilitate direct, or indirect detection and/or quantification of binding. Examples of labels which permit direct measurement of immunocomplexes include radiolabels, such as $^3H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the second antibody is labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Alternatively, the antibody may be unlabeled. In this case, a labeled second receptor-specific compound is employed which binds to the second antibody. Such a second receptor-specific compound can be labeled in any of the above manners. It is possible to select such compounds such that multiple compounds bind each molecule of bound second receptor. Examples of second antibody/second receptor-specific molecule pairs include antibody/anti-antibody and avidin (or streptavidin)/biotin. Since the resultant signal is thus amplified, this technique may be advantageous where only a small amount of Actin protein or fragment thereof is present. An example is the use of a labeled antibody specific to the second antibody. The volume, composition and concentration of second antibody solution provides for measurable binding to the Actin protein already bound to the first antibody. Generally, the same volume as that of the sample is used: from about 0.001 to 1 ml is sufficient, usually about 0.1 ml sufficing. The concentration will generally be sufficient to saturate all Actin protein potentially bound to first antibody.

The concentration generally will be about 0.1 to 50 µg/ml, preferably about 1 µg/ml. The solution containing the second antibody is generally buffered in the range of about pH 6.5-9.5. The solution may also contain an innocuous protein as previously described. The incubation time should be sufficient for the labeled ligand to bind available molecules. Generally, from about 0.1 to 3 hr is sufficient, usually 1 hr sufficing. After the second antibody has bound, the insoluble support is generally again washed free of non-specifically bound second receptor, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490-495 nm is conveniently measured with a spectrophotometer.

Depending on the particular nature of the antibody based assay employed, it may be desirable to employ antibodies that are capable of distinguishing between the various Actin protein forms and fragments thereof. For example, in a Western blot assay a single type of antibody that recognizes all of the various Actin protein fragments and the native Actin protein itself may be employed, since the various fragments and native protein are pre-separated, e.g. by gel electrophoresis. However, where the various fragments and native protein are not separated prior to detection, e.g. in the competitive and sandwich assays described above, it is desirable to use a plurality of antibodies which are capable of specifically recognizing only a single Actin protein species of interest, with substantially no cross-reactivity with other Actin protein species or fragments that may be present in the sample.

In the subject methods, the sample or fractions thereof are at least assayed for the presence or absence of the low molecular Actin protein fragments or species, and often times the native species as well, where the assay may be a direct assay for low molecular weight fragments or an indirect assay for low molecular weight fragments, as indicated above. In some embodiments, qualitative results are sufficient. Thus, one may be interested in identifying the presence or absence of the low molecular weight Actin protein fragments as a marker for the disease involving abnormal levels of cellular apoptosis, e.g. in the diagnostic methods described above. Alternatively, one may be interested in making a qualitative determination, to measure for instance of the total amount of Actin protein species present, or to determine the ratio of the low molecular weight species to the native species. In many embodiments, the assays employed at least provide semi-quantitative detection of the various molecular weight Actin protein species, and not just qualitative detection.

In assaying for low molecular weight Actin protein fragments or species in the subject methods, one may look for: (a) the presence or absence of the low molecular weight Actin protein fragments; (b) the pattern of the low molecular weight Actin protein fragments and, optionally full length Actin protein (where by pattern is meant the presence of each fragment and, optionally relative amount of each fragment); (c) the ratio of the amounts of the various low molecular weight Actin protein species to each other and/or to the full length Actin protein; and the like; (d) the relative amount of high molecular weight or native Actin protein to all Actin protein species in the sample; etc.

In many embodiments, based on the presence or absence of the various molecular weight Actin protein species, and usually the semi-quantitative values obtained for each of the species of interest, the disease involving abnormal levels of cellular apoptosis activity in the subject from which the sample was derived is characterized. This broad category of embodiments includes those in which the low molecular weight Actin protein species are directly assayed, e.g., those methods where: (a) the simple presence or absence of low molecular weight species is used to characterize the disease; (b) the ratio of low molecular weight species to high molecular weight species is used to characterize the disease; and (c) the pattern or amounts of two or more different low molecular weight species is used to characterize the disease; etc.

In yet other embodiments, e.g. those based on assays which indirectly determine the presence or absence of low molecular weight Actin protein species, the relative amounts of the various Actin protein species in the sample to each other, e.g., the relative amount of native or high molecular weight Actin protein to the total amount of Actin protein, i.e., native Actin protein and fragment species thereof, in the sample is used to characterize the disease involving abnormal levels of cellular apoptosis activity in the subject.

In yet other embodiments, e.g. those based on the quantification of all Actin protein species present, the amount of Actin protein species present may be compared to values obtained from normal (i.e., healthy) individuals in order to characterize the disease involving abnormal levels of cellular apoptotic activity in the subject.

Characterization of disease involving abnormal levels of cellular apoptosis activity according to the subject methods typically involves comparing the results obtained to a table or other source of predetermined values or reference values which provide information about the disease activity in the host, e.g. that positively or negatively correlate to the presence of the disease involving abnormal levels of cellular apoptosis, a particular stage of the disease involving abnormal levels of cellular apoptosis, and the like. For example, a table of values may be consulted in this step, where the table comprises representative values for the high and low molecular weight proteins as found in patients suffering from the disease involving abnormal levels of cellular apoptosis of interest. The values may be presented in numerical form, in picture form (e.g. as bands on a gel), and the like. By comparing the observed values with these reference values, e.g. by comparing a pattern of the Actin protein species in the sample to a reference pattern or picture, characterization of the disease activity, e.g. confirmation of diagnosis, determination of disease state, etc., is readily made. In other embodiments, the ratio of two or more of the different species and/or full length Actin protein is then compared to reference list of ratios to characterize the disease involving abnormal levels of cellular apoptosis activity.

As summarized above, the subject methods are methods of characterizing disease involving abnormal levels of cellular apoptosis activity in a host. The term characterizing is used broadly to refer to derivation of any type of information about the state of the disease involving abnormal levels of cellular apoptosis in the host. As such, the subject methods may be used to confirm an initial diagnosis of disease involving abnormal levels of cellular apoptosis, to determine the state of the disease in a patient known to have the disease involving abnormal levels of cellular apoptosis, to monitor the progression of the disease, to predict the occurrence of an attack, and the like. Where the subject invention is employed to confirm an initial diagnosis, a sample is obtained from subject suspected of having the disease involving abnormal levels of cellular apoptosis (where the subject may be identified as described supra). For example, the sample is assayed for the presence of the high and low molecular weight Actin protein species, a ratio of the two species is derived and then compared to reference values, where the reference values correlate given ratios to the presence or absence of the disease involving abnormal levels of cellular apoptosis.

The subject methods are also employed to determine the stage of the disease involving abnormal levels of cellular apoptosis in the subject. In other words, the subject disease involving abnormal levels of cellular apoptosis activity characterization methods may be employed to determine whether the patient is in a remission stage, a chronic stage etc. For example, the subject methods may be employed to determine a clinical remission of cancer. To determine the stage of the disease, the observed values for the one or more Actin protein species, and ratios where desired, in the assayed sample are compared to reference values that are correlated to a particular stage of disease involving abnormal levels of cellular apoptosis, e.g. prostate cancer.

In yet other embodiments, characterization of disease activity yields information concerning the disease progression in the patient, e.g. whether disease progression has accelerated or slowed. For example, the initial characterization date, i.e. the amount of high and low molecular forms in the patient derived sample, could be employed as a baseline value to evaluate subsequent testings, e.g. at some time following the initial testing, e.g. 3 months. If the amount of low molecular weight Actin protein species decreases in subsequent testing, this indicates that the disease is not progressing and may be resolving. Alternatively, if the amount of low molecular weight Actin protein species increases, this indicates that the disease is progressing in severity.

The characterization data obtained from the subject methods may also be used to determine whether a particular therapeutic regimen is having positive affects with respect to the progression of the disease. For example, at various time periods during the course of treatment, the subject methods may be performed to obtain a reading of the amount of high and low molecular weight forms of the Actin protein species of interest. If the amount of the low molecular weight form of the Actin protein is increasing, this indicates that the treatment regimen is not having the desired effect. Alternatively, if the amount of the low molecular weight form of the Actin protein is decreasing, this indicates that the treatment regimen is working.

In yet other embodiments, the characterization data obtained from the subject methods is used to predict when a disease involving abnormal levels of cellular apoptosis attack, e.g., viral re-activation, may occur. In this embodiment, the characterization data is compared to reference values, where some of the reference values correlate to the occurrence of an attack.

Depending on the particular test protocol, the subject methods may further include one or more additional assays associated with the disease involving abnormal levels of cellular apoptosis of interest. For example, one may couple the subject methods with assays that measure changes in the levels of one or more inflammatory enzymes (e.g., elastase, caspases).

Also provided by the subject invention are kits for use in carrying out the subject methods. The kits at least comprise reagents necessary for carrying out the Actin protein species detection assays, where such kits may include: Actin protein specific antibodies and/or immunoassay devices comprising the same; members of a signal producing system, such as antibodies, enzyme substrates, and the like; various buffers for use in carrying out the subject detection assays; and the like. The kits may further include one or more reagents necessary for preparation of the patient derived sample, such as heparin, Ficoll-Hypaque, lysing buffer, protease inhibitor, and the like, e.g. where the patient sample is PBMC derived, etc. In addition, the subject kits may further include one or more components employed in fractionation of the sample, such as an electrophoretic medium or precursors thereof, e.g. dried precursors of polyacrylamide gels, one or more buffer mediums or components thereof, and the like. In most embodiments, the kits further include at least an information storage and presentation medium that contains reference data with which assay results may be compared in order to diagnose and/or characterize the disease involving abnormal levels of cellular apoptosis activity in the subject being assayed, i.e. reference data that includes various values of the high and low molecular weight Actin protein species and relates these values to the presence or absence of disease involving abnormal levels of cellular apoptosis and/or the activity of the disease in the host. The information storage and presentation medium may be in any convenient form, such as a printed information on a package insert, an electronic file present on an electronic storage medium, e.g. a magnetic disk, CD-ROM, and the like. In yet other embodiments, the kits may include alternative means for obtaining reference data, e.g. a website for obtaining the reference data "on-line." The kits may further include means for obtaining the patient sample, e.g. a syringe. The subject kits further typically include instructions for carrying out the subject methods, where these instructions may be present on a package insert and/or the packaging of the kit. Finally, the kit may further include one or more reagents from an additional biochemical assay which is used to detect the presence of and/or characterize the disease involving abnormal levels of cellular apoptosis of interest. For example, where SARS is the disease involving abnormal levels of cellular apoptosis of interest, the kits may further include one or more reagents from an assay designed to detect the presence of antibodies or DNA fragments specific for the infectious agent.

The following examples are offered by way of illustration and not by way of limitation.

EXPERIMENTAL

I. Analysis and Quantification of Low and High Molecular Weight Actin Protein Species in Serum Samples Study subjects were from the Medical Service of the European Commission. Subjects-were selected based upon their having recently traveled to an returned from countries, mostly in Asia, where SARS cases have been detected and the presence of the SARS-associated Coronavirus has been established. At the time of blood sampling, patient symptoms were evaluated and recorded.

i. Serum Collection

Venous blood was collected by standard venipuncture methods. The blood was allowed to clot at room temperature and the serum was collected by centrifugation. Sera were stored at −70 C. until assayed.

ii. Actin Protein Species Detection

Analysis of Actin protein and Actin protein fragment proteins was performed using SDS-PAGE and Western blotting. Two microliters of serum were added to 8 microliters of phosphate buffered saline (PBS), to which was then added 2×SDS-PAGE gel sample dye that included a tracking dye. The sample plus dye was then heated to 95° C. for five minutes to denature the proteins. The denatured samples were then subjected to standard SDS-PAGE using a four percent stacking gel and ten percent separating gel Also included in the first lane of each gel was a molecular weight marker, pre-stained to be visible as it migrated during the course of electrophoresis (Bio-Rad Laboratories). The gel was electrophoresed until the tracking dye had migrated to the bottom of the gel.

The gel was then transferred to a PVDF membrane (Bio-Rad Laboratories) using a semi-dry transfer system (Amersham-Pharmacia Biotech). Transfer was performed at an average current of 0.8 milliamp per $cm^2$ of gel (or 100 mA for a standard 15 cm×8 cm gel) for two hours.

After transfer was complete (as determined by the visual agreement of the transfer of the color from the pre-stained molecular weight markers to the membrane), the membrane was allowed to dry thoroughly at room temperature for at least one hour.

Western blotting was performed using the following format: The membrane was first wet with a minimum volume of 100 percent methanol (according to the manufacturer's instruction). Then a solution of five percent non-fat dry milk (5% NFDM) was used to 'block' the membrane ('blocking buffer') to eliminate non-specific background binding of antibody. The membrane was 'blocked' for one hour with gentle shaking on an orbital shaker.

The blocking buffer was discarded and fresh blocking buffer was added in the amount of approximately 0.1 mL per $cm^2$ of membrane, to which was added the primary antibody (rabbit anti-Actin protein; Sigma Corporation) at a 1:500 dilution according to the manufacturer's recommendations. The membrane was allowed to react with the primary antibody for one hour with gentle shaking on an orbital shaker. The primary antibody solution was then discarded and the membrane was washed three times with 25 mLs per wash of phosphate buffered saline (PBS, pH=7.4) plus 0.1% Tween 20 (polyoxyethylene sorbitan monolaurate; Sigma Corporation). Each wash was five minutes in length, with shaking, and the each time the solution was discarded.

Fresh blocking buffer was added in the amount of approximately 0.1 mL per $cm^2$ of membrane, to which was added the secondary antibody (goat anti-rabbit antibody, conjugated to horseradish peroxidase (GAR-HRP); Bio-Rad Laboratories) at a 1:2000 dilution according to the manufacturer's recommendations. The membrane was allowed to react with the secondary antibody for thirty minutes with gentle shaking on an orbital shaker. The secondary antibody solution was discarded and the membrane was washed three times with 25 mLs per wash of phosphate buffered saline (PBS, pH=7.4) plus 0.1% Tween 20. Each wash was five minutes in length, with shaking, and the each time the solution was discarded.

Color development was performed using the Opti4-CN kit (Bio-Rad Laboratories) according to the manufacturer's recommendations. Color development was allowed to proceed for 15 minutes and the membrane was then rinsed in copious changes of water and allowed to dry at room temperature. The results are shown in FIG. 1. The membrane was then analyzed by densitometry and quantification of Actin protein and Actin protein fragment proteins present was performed using specialized software (Quantity One; Bio-Rad Laboratories).

iii. Actin Protein Species Quantification

The concentration of the total Actin protein species present in the serum is performed by a competition assay using Surface Plasmon Resonance (SPR). Briefly, polyclonal antibodies to Actin protein (recognizing native Actin protein species and fragments thereof) are combined with a sample of serum. To this is then added a known amount of native Actin protein that has been electrostatically attached to colloidal gold nanoparticles (hereafter Actin-CG).

Any Actin protein species present in serum will compete with the Actin-CG particles for the anti-Actin antibody. Therefore, increasing levels of Actin protein species in the serum will in turn decrease the amount of interaction of Actin-CG with the antibody, resulting in a lower number of antibody molecules to bind to Actin-CG. Thus the amount of antibody bound to Actin-CG is inversely proportional to the amount of Actin protein species present in the sample. Using the technique of Surface Plasmon Resonance (SPR), the amount of antibody bound to Actin-CG may be measured optically as a function of the decrease in the reflected light from the Actin-CG particles upon binding the antibody. Thus the change in reflected light is inversely proportional to the amount of antibody bound to Actin-CG.

The quantification of Actin protein species was performed using an automated clinical chemistry analyzer, the Roche COBAS Mira.

B. Analysis of Results

FIG. 1 represents a densitometric scan of a Western blot detecting Actin protein protein and Actin protein protein fragments. Native G-Actin protein is clearly visible at a molecular weight of 42 kDa as are the fragments of 27 kDa and 15 kDa, also indicated with arrows. Patient #3 has clearly defined Actin protein fragments. According to this analysis, Patient #3 would be said to have a disease involving abnormally elevated levels of cellular apoptotic activity.

Table 1 details the quantification of total Actin protein species present in serum using surface plasmon resonance as detected using an indirect assay and the Roche COBAS Mira instrumentation system. In patients #3, #12, and #17, abnormally high levels of total Actin protein species were detected. Subsequently all specimens were analyzed by the polymerase chain reaction technique for the presence of certain infectious agents. In these three cases (~3, ~12 and #17), infection with Mycoplasma species was detected. In two patients (#6 and #8), abnormally low levels of total Actin protein species were detected. No infectious agents were detected in these patients. However, screening for various tumor markers of broad indication (e.g., carcinoembryonic antigen (CEA)) may be in order.

TABLE 1

Quantification of Total Actin Protein Species in Serum Using Surface Plasmon Resonance (SPR)

| Specimen No. | Amount of Actin (ug/mL)* | Clinical Indication | Detection of Other Infectious Diseases Present** |
|---|---|---|---|
| 1 | 4.3 | Negative | None |
| 2 | 4.5 | Negative | None |
| 3 | 7.9 | Abnormal High | Mycoplasma hyorhinis |
| 4 | 3.1 | Negative | None |
| 5 | 2.4 | Negative | None |
| 6 | 1.7 | Abnormal Low | None |
| 7 | 2.4 | Negative | None |
| 8 | 1.0 | Abnormal Low | None |
| 9 | 2.3 | Negative | None |
| 10 | 5.8 | Negative | None |
| 11 | 3.0 | Negative | None |
| 12 | 7.4 | Abnormal High | Mycoplasma fermentans |
| 13 | 3.2 | Negative | None |
| 14 | 5.5 | Negative | None |
| 15 | 6.0 | Negative | None |
| 16 | 2.5 | Negative | None |
| 17 | 8.1 | Abnormal High | Mycoplasma fermentans |
| 18 | 3.2 | Negative | None |
| 19 | 2.1 | Negative | None |
| 20 | 4.5 | Negative | None |

*Normal Range Cut-Off Values for Total Actin Protein Species: 2.1 ug/mL to 7.2 ug/mL
**The detection of other infectious diseases present represents the determination by the PCR process of the presence of the following infectious agents: Mycoplasma species, Chlamydia species, all known Herpesviruses, and SARS-CoV The above results demonstrate that both the relative amount of Actin protein and related protein fragments as well as the total amount of Actin protein species may be objectively determined and may be used to to characterize the disease involving abnormal levels of cellular apoptosis activity in a subject.

It is evident from the above results and discussion that relatively simple and rapid methods are provided for diagnosing and/or characterizing disease involving abnormal levels of cellular apoptosis activity in a subject are provided. With the subject methods, accurate diagnosis of the disease involving abnormal levels of cellular apoptosis condition, as well the identification of the stage and/or progression of the disease involving abnormal levels of cellular apoptosis condition, may be obtained. As such, the subject methods provide for more accurate diagnostic and/or treatment regimens. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of characterizing an infectious disease involving abnormal levels of cellular apoptosis activity in a human subject, said method comprising:
    (a) obtaining a serum sample from said subject;
    (b) identifying a pattern of low molecular weight Actin protein fragments in said serum sample; and
    (c) using said pattern to characterize said infectious disease involving abnormal levels of cellular apoptosis activity in said subject.

2. The method according to claim 1, wherein said infectious disease is SARS.

3. The method according to claim 1, wherein said serum sample is produced by obtaining a blood sample, allowing said blood sample to clot and separating serum from said clot to produce said serum sample.

* * * * *

UNITED STATES PATENT AND TRADEMARK OFFICE
CERTIFICATE OF CORRECTION

| | | |
|---|---|---|
| PATENT NO. | : 7,713,515 B2 | Page 1 of 1 |
| APPLICATION NO. | : 10/855879 | |
| DATED | : May 11, 2010 | |
| INVENTOR(S) | : Englebienne et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1509 days.

Signed and Sealed this
Twenty-fifth Day of January, 2011

David J. Kappos
*Director of the United States Patent and Trademark Office*